(12) United States Patent
Knauf et al.

(10) Patent No.: US 9,284,255 B2
(45) Date of Patent: Mar. 15, 2016

(54) METHOD FOR PRODUCING NITROBENZENE BY ADIABATIC NITRIDING

(71) Applicant: Bayer MaterialScience AG, Leverkusen (DE)

(72) Inventors: Thomas Knauf, Dormagen (DE); Alexandre Racoes, Krefeld (DE); Wolfgang Dohmen, Duisburg (DE); Antoni Mairata, Dusseldorf (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 14/413,277

(22) PCT Filed: Jul. 23, 2013

(86) PCT No.: PCT/EP2013/065502
§ 371 (c)(1),
(2) Date: Jan. 7, 2015

(87) PCT Pub. No.: WO2014/016289
PCT Pub. Date: Jan. 30, 2014

(65) Prior Publication Data
US 2015/0175521 A1 Jun. 25, 2015

(30) Foreign Application Priority Data
Jul. 27, 2012 (EP) .................... 12178160

(51) Int. Cl.
*C07C 201/00* (2006.01)
*C07C 201/06* (2006.01)
*C07C 201/08* (2006.01)

(52) U.S. Cl.
CPC ............. *C07C 201/06* (2013.01); *C07C 201/08* (2013.01)

(58) Field of Classification Search
CPC ........................... C07C 201/06; C07C 201/08

USPC .......................................... 568/939
See application file for complete search history.

(56) References Cited

U.S. PATENT DOCUMENTS

| | | | |
|---|---|---|---|
| 2,256,999 | A | 9/1941 | Castner |
| 4,091,042 | A | 5/1978 | Alexanderson et al. |
| 5,313,009 | A | 5/1994 | Guenkel et al. |
| 5,616,818 | A | 4/1997 | Pirkl et al. |
| 5,763,697 | A | 6/1998 | Hermann et al. |
| 7,326,816 | B2 | 2/2008 | Knauf et al. |
| 7,344,650 | B2 | 3/2008 | Knauf et al. |
| 7,763,759 | B2 | 7/2010 | Knauf et al. |
| 7,731,624 | B2 | 8/2010 | Rausch et al. |
| 8,357,827 | B2 | 1/2013 | Munnig et al. |
| 2003/0055300 | A1 | 3/2003 | Chrisochoou et al. |
| 2010/0280271 | A1 | 11/2010 | Sommer et al. |
| 2011/0196177 | A1* | 8/2011 | Munnig et al. ................ 568/939 |
| 2013/0204043 | A1 | 8/2013 | Knauf et al. |

FOREIGN PATENT DOCUMENTS

| | | |
|---|---|---|
| DE | 1129466 | 5/1962 |
| DE | 102009005324 A1 | 7/2010 |
| EP | 0373966 A2 | 6/1990 |
| EP | 0436443 A2 | 7/1991 |
| EP | 0976718 A2 | 2/2000 |
| EP | 1132347 A2 | 9/2001 |
| EP | 2155655 B1 | 8/2011 |
| WO | 2010051616 A1 | 5/2010 |

\* cited by examiner

*Primary Examiner* — Sikarl Witherspoon
(74) *Attorney, Agent, or Firm* — Donald R. Palladino

(57) ABSTRACT

The invention relates to an adiabatic process for producing nitrobenzene by nitrating benzene with sulphuric acid mixtures and nitric acid mixtures using a stoichiometric excess of benzene and reusing non-reacted benzene, the content of the aliphatic organic compounds in the feed benzene being limited, by the targeted evacuation of aliphatic organic compounds to at least one step in the process, to a content of less than 1.5 mass-%, in relation to the total amount of feed benzene.

15 Claims, 2 Drawing Sheets

METHOD FOR PRODUCING NITROBENZENE BY ADIABATIC NITRIDING

CROSS-REFERENCE TO RELATED APPLICATIONS

This application is a National Phase Application of PCT/EP2013/065502, filed Jul. 23, 2013, which claims priority to European Application No.: 12178160.3, filed Jul. 27, 2012, each of which being incorporated herein by reference.

FIELD

The invention provides an adiabatic process for the preparation of nitrobenzene by nitrating benzene with mixtures of sulfuric and nitric acids using a stoichiometric excess of benzene and re-using unreacted benzene, wherein the content of aliphatic organic compounds in the starting benzene is limited to less than 1.5 wt %, based on the total weight of starting benzene, by specifically removing aliphatic organic compounds at at least one point during the process.

BACKGROUND

The present invention relates to a continuous process for the preparation of nitrobenzene by the adiabatic nitration of benzene with a mixture of sulfuric and nitric acids (so-called 'mixed acid'). Such a process was first claimed in U.S. Pat. No. 2,256,999 and is described in more modern embodiments in U.S. Pat. No. 4,091,042, U.S. Pat. No. 5,313,009 and U.S. Pat. No. 5,763,697.

A common feature of the adiabatic processes described is that the starting materials, benzene and nitric acid, are reacted in a large excess of sulfuric acid, which absorbs the heat of reaction evolved and the water formed in the reaction.

The reaction procedure generally involves combining the nitric acid and sulfuric acid to give so-called 'nitrating acid' (also called 'mixed acid'). Benzene is metered into this nitrating acid. The reaction products are essentially water and nitrobenzene. In the nitration reaction, benzene is used in at least the stoichiometric amount, but preferably in 2% to 10% excess, based on the molar amount of nitric acid. In accordance with the state of the art, the crude nitrobenzene formed in the reaction apparatuses and separated from the acid phase in the phase separation apparatus is washed and worked up by distillation, as described e.g. in EP 1 816 117 B1 (page 2, lines 26 to 42), U.S. Pat. No. 4,091,042 (cf. above) or U.S. Pat. No. 5,763,697 (cf. above). A characteristic feature of this work-up is that, after washing, unreacted excess benzene is separated from nitrobenzene in a final distillation and re-used in the nitration reaction as recycle benzene, which also comprises low-boiling non-aromatic organic compounds (so-called 'low boilers') (cf DE 10 2009 005 324 A1). The treatment of the off-gas from the adiabatic nitration reaction is described in EP 0 976 718 B1. The off-gas from the acid circuit and from the final crude nitrobenzene is drawn off, combined and passed through a $NO_x$ absorber to recover dilute nitric acid, which is recycled into the reaction. The sulfuric acid, referred to as recycle acid, is concentrated in a flash evaporator and freed of organics as far as possible. Traces of high-boiling organics, e.g. nitrobenzene, dinitrobenzene and nitrophenols, remain in the recycle acid and are thus also recycled into the reaction.

The quality of an adiabatic process for the nitration of aromatic hydrocarbons is defined on the one hand by the content of unwanted reaction by-products in the product, which are formed by multiple nitration or oxidation of the aromatic hydrocarbon or the nitroaromatic. In the preparation of nitrobenzene one strives to minimize the content of dinitrobenzene and nitrophenols, particularly trinitrophenol (picric acid), which is classified as explosive.

The quality of an adiabatic process is defined on the other hand by use of the smallest possible amount of energy to prepare the nitrobenzene. This is assured inter alia by utilizing the adiabatic heat of reaction to concentrate the sulfuric acid or by minimizing the stoichiometric excess of benzene required in the reaction, based on nitric acid, in order not to expend unnecessary amounts of energy on the washing and final distillation of the crude nitrobenzene.

To obtain nitrobenzene with particularly high selectivities, the nature of the mixed acid to be used has been stipulated in detail (EP 0 373 966 B1, EP 0 436 443 B1 and EP 0 771 783 B1) and it has been indicated that the content of by-products is determined by the value of the maximum temperature (EP 0 436 443 B1, column 15, lines 22 to 25). It is also known that a high initial conversion is advantageous for a high selectivity and that this is achieved when optimum intermixing is applied at the start of the reaction (EP 0 771 783 B1, paragraphs [0012] to [0014]).

Outstanding selectivities are obtained when the chosen initial reaction temperature is very low (WO 2010/051616 A1), although this is tantamount to increasing the reaction time several fold. A high space-time yield is advantageous for the industrial application of a process since this makes it possible to construct compact reaction equipment distinguished by low capital expenditure in relation to capacity. This procedure is therefore counterproductive.

As regards the quality of the benzene starting material in the adiabatic preparation of nitrobenzene, EP 2 246 320 A1 describes that, depending on its source, commercially available benzene can be contaminated to a greater or lesser extent. Typical impurities are other aromatics, especially toluene and xylene, which can each be present in amounts of up to 0.05 wt % in benzene of common purity. Other impurities typical for benzene are anon-aromatic organic compounds, which can account for a total of up to 0.07 wt %. Cyclohexane (up to 0.03 wt %) and methylcyclohexane (up to 0.02 wt %) are cited in particular here. In the concentrations mentioned, the impurities described above have either no or only a very slight adverse effect on the subsequent steps of the MDI process chain (MDI=di- and polyisocyanates of the diphenylmethane series), e.g. by slightly disturbing the waste water and off-gas treatment in the nitrobenzene process due to non-aromatic organics in benzene. A laborious purification of the benzene for use in the MDI process chain is therefore deemed excessive and can be omitted. EP 2 246 320 A1 does not go into the non-aromatic organic compounds in the benzene which is separated from the crude product at the end of the reaction and recycled into the nitration (so-called 'recycle benzene').

DE 10 2009 005 324 A1 discloses that technical-grade benzene conventionally comprises 0.01% to 0.5% of low-boiling non-aromatic organic compounds (low boilers). However, the common benzene nitration processes do not use technical-grade benzene as such, but rather a mixture of recycle benzene and technical-grade benzene, so that the content of low boilers in the benzene actually used can be appreciably higher than in commercially available technical-grade benzene. By way of example, DE 10 2009 005 324 A1 discloses a value of 5% (paragraph [0007]). According to the teaching of this specification, a low boiler content of this magnitude is still not disadvantageous in the actual nitration. DE 10 2009 005 324 A1 only goes into problems with the subsequent phase separation (paragraph [0008]). A special phase separation method using a pressure-holding siphon is proposed for solving these problems.

EP 2 155 655 B1 only goes into aromatic impurities (alkyl-substituted aromatics) in the benzene.

DE-B 1 129 466 describes a process for the mononitration of technical-grade benzene, xylene and toluene comprising the customary amounts of aliphatic hydrocarbons, wherein the first runnings of unreacted aromatic obtained in the distillation of the nitroaromatic, which are rich in aliphatic impurities, are mixed with fresh aromatic and fed into the nitration, and the first runnings obtained each time are recycled as many times as desired. (Where benzene is the starting material, the first runnings of aromatic in this specification correspond to the aforementioned recycle benzene.) Those skilled in the art therefore infer from this specification the technical teaching that an increased proportion of aliphatic impurities in the aromatic to be used does not adversely affect the nitration.

EP 0 976 718 A2 discloses a process in which the off-gas is treated in an $NO_x$ absorber and then burnt There is no mention of the resulting benzene losses and the low boilers removed in this way.

It is true that the described processes of the state of the art succeed in preparing a nitrobenzene having a low content of by-products, i.e. only comprising about 100 ppm to 300 ppm of dinitrobenzene and 1500 ppm to 2500 ppm of nitrophenols, it being possible for picric acid to make up 10 wt % to 50 wt % of the nitrophenols. The processes are also distinguished by a high space-time yield.

Apart from the purity of the crude nitrobenzene, it is of decisive importance for industrial production that the preparation of the nitroaromatic be capable of being carried out in the most compact reaction equipment possible and under favourable energy conditions (such as a small excess of benzene). It is also desirable to have the most favourable raw materials possible, although they may comprise unwanted secondary components.

Impurities in the freshly introduced benzene and/or in the recycle benzene reduce the total available concentration of benzene, thereby slowing the reaction down. The reduced benzene concentration can result in the use of an excessive amount of nitric acid. This in turn increases the amount of unwanted polynitrated products and $NO_x$ gases, the latter resulting in the formation of further by-products. Critical impurities in this sense are especially aliphatic organic compounds (low boilers, cf. above). These can outgas together with $NO_3$ gases during the reaction and hence cause further disadvantages, e.g. a poorer intermixing of the reactants and a reduced reaction volume. There was therefore a need for a method of minimizing, or ideally eliminating altogether, the content of aliphatic organic compounds in the benzene actually used in an adiabatic nitration process.

SUMMARY

With the above in mind, the present invention is concerned with minimizing the adverse effect of aliphatic organic compounds. Two fundamental variants were developed for this purpose:

In the first variant the present invention provides a continuous adiabatic process for the preparation of nitrobenzene by the nitration of benzene in a nitration unit, wherein a) a benzene-containing stream (a.1), comprising at least 90 wt %, preferably at least 95 wt % and particularly preferably at least 99 wt % of benzene, based in each case on the total weight of (a.1), is reacted in a reactor with a mixture of sulfuric acid (a.2) and nitric acid (a.3) under adiabatic conditions, the benzene being used in a stoichiometric excess, based on nitric acid (a.3), preferably of 2.0% to 20%, particularly preferably of 5.0% to 10% of theory, b) the process product obtained in step a) is separated in a phase separation apparatus into an aqueous phase (b.1) comprising sulfuric acid and an organic phase (b.2) comprising nitrobenzene, c) the aqueous phase (b.1) obtained in step b) is concentrated by evaporation of the water to give an aqueous phase (c.1) having a higher sulfuric acid concentration than (b.1), and all or part of the phase (c.1) being recycled into step a) and used as a component of (a.2), and d) the organic phase (b.2) obtained in step b) is worked up to pure nitrobenzene (d.1), preferably by washing with aqueous media and subsequent rectification, to give a benzene-containing stream (d.2) (so-called 'recycle benzene') which comprises preferably 40.0 wt % to 99.9 wt %, particularly preferably 60.0 wt % to 99.9 wt %, very particularly preferably 80.0 wt % to 99.9 wt % and extremely particularly preferably 90.0 wt % to 99.9999 wt % of benzene, based in each case on the total weight of (d.2), and all or part of which is used as a component of (a.1) in the nitration unit of step a), and wherein
aliphatic organic compounds are specifically removed from the process at at least one point so that only such a benzene-containing stream (a.1) having the following content of aliphatic organic compounds is fed into the reactor: less than 1.5 wt %, preferably less than 0.50 wt %, particularly preferably less than 0.20 wt % and very particularly preferably less than 0.10 wt %, based in each case on the total weight of (a.1).

In the second variant the present invention provides an adiabatic process for the preparation of nitrobenzene by the nitration of benzene in a series of two nitration units (100, 200) each having at least one reactor (1, 1*), wherein a) exclusively benzene (a.1.1) having a content of aliphatic organic compounds of less than 1.5 wt %, preferably of less than 0.50 wt %, particularly preferably of less than 0.20 wt % and very particularly preferably of less than 0.10 wt %, based in each case on the total weight of (a.1.1), is reacted in the reactor (1) of the first, continuously operating nitration unit (100) with a mixture of sulfuric acid (a.2.1) and nitric acid (a.3.1) under adiabatic conditions, the benzene being used in a stoichiometric excess, based on nitric acid (a.3.1), preferably of 2.0% to 20%, particularly preferably of 5.0% to 10% of theory, b) the process product obtained in step a) is separated in a phase separation apparatus (2) into an aqueous phase (b.1.1) comprising sulfuric acid and an organic phase (b.2.1) comprising nitrobenzene, c) the aqueous phase (b.1.1) obtained in step b) is concentrated by evaporation of the water to give an aqueous phase (c.1.1) having a higher sulfuric acid concentration than (b.1.1), and all or part of the phase (c.1.1) being recycled into step a) and used as a component of (a.2.1), and d) the organic phase (b.2.1) obtained in step b) is worked up to pure nitrobenzene (d.1.1) to give a benzene-containing stream (d.2.1) which comprises preferably 40.0 wt % to 99.9 wt %, particularly preferably 60.0 wt % to 99.9 wt %, very particularly preferably 80.0 wt % to 99.9 wt % and extremely particularly preferably 90.0 wt % to 99.9999 wt % of benzene, based in each case on the total weight of (d.2.1), and wherein the benzene-containing stream (d.2.1) is reacted in a reactor (1*) of the second, continuously or discontinuously operating nitration unit (200) with a mixture of sulfuric acid (a.2.2) and nitric acid (a.3.2) under adiabatic conditions to give nitrobenzene, the benzene being used in a stoichiometric excess, based on nitric acid (a.3.2), preferably of 2.0% to 20%, particularly preferably of 5.0% to 10% of theory, and the nitrobenzene formed in this way then being worked up to pure nitrobenzene.

DETAILED DESCRIPTION

Figure 1:
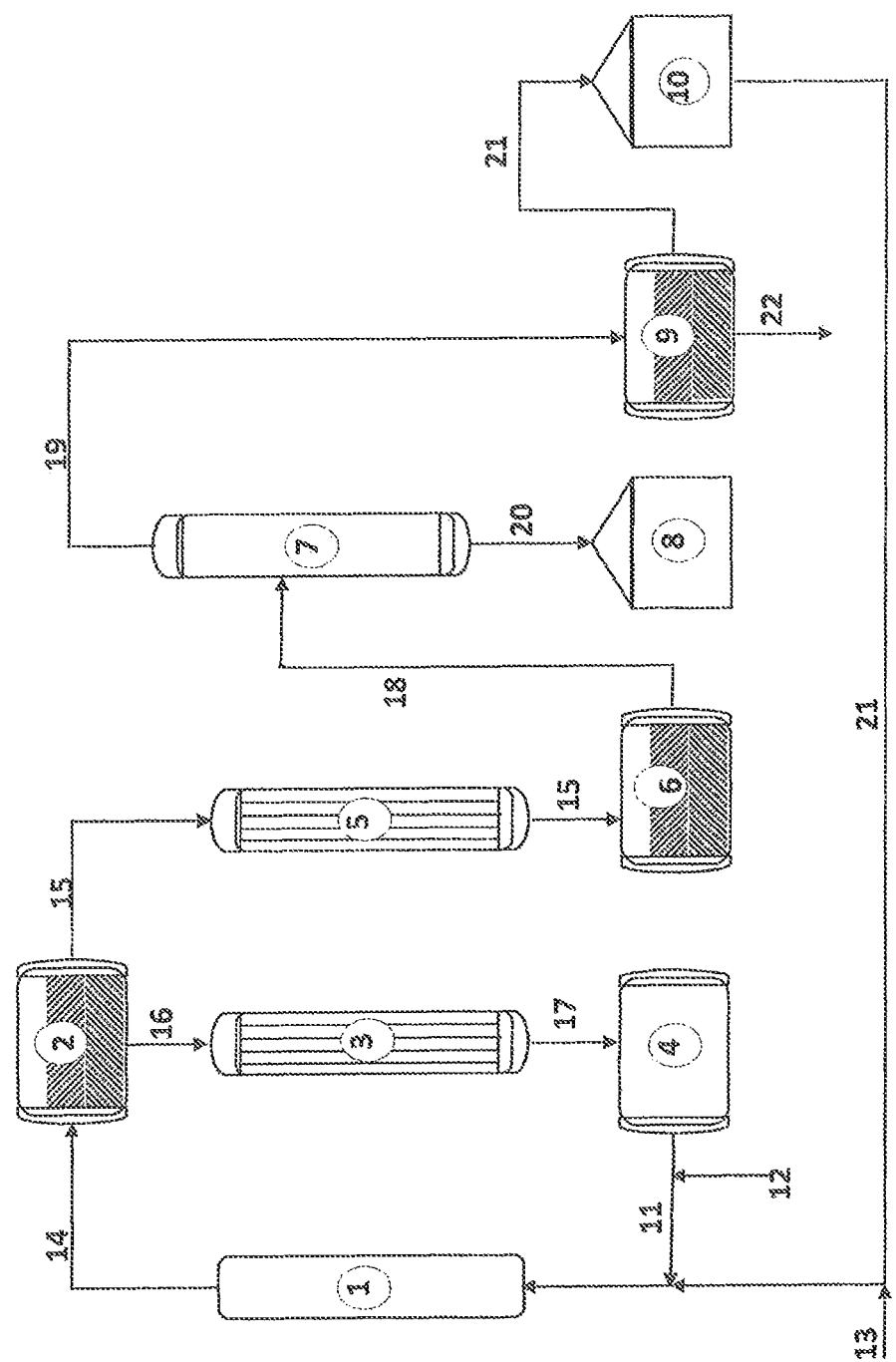
FIG. 1 shows a process in which only the first nitration unit (primary unit) of FIG. 2 is used.

According to the invention a nitration unit comprises at least one nitration reactor and at least one phase separation apparatus and the peripheral devices necessary for their operation, such as pipelines, pumps, optionally heat exchangers, etc. In the embodiment with a series of two nitration units (100, 200), the apparatuses required for further processing of the organic phase comprising nitrobenzene, obtained after phase separation of the crude nitration product, and of the aqueous phase comprising sulfuric acid (evaporation apparatus and working-up devices such as washers and a distillation column) can be utilized by both nitration units (100, 200) together (cf. also FIG. 2). If there is only one nitration unit present (cf. also FIG. 1), these apparatuses are of course also part of said unit.

The benzene excess based on nitric acid of 2.0% to 20%, preferably of 5.0% to 10% of theory, refers to the molar ratio of benzene and nitric acid. Theoretically one mol of nitric acid reacts with one mol of benzene to give one mol of nitrobenzene.

In terms of the present invention, aliphatic organic compounds preferably comprise cyclohexane, heptane, methylcyclohexane, bicycloheptane, isomers of dimethylcyclopentane, ethylcyclopentane, pentane, cyclopentane and 2-methylhexane. According to the invention, the content of aliphatic organic compounds in the benzene-containing stream (a.1) (so-called 'starting benzene') must be monitored. Analytical measurements are required for this purpose. The fresh benzene in the tank, the starting benzene and the recycle benzene (d.2) are measured, preferably by taking samples at the appropriate points and analysing them by gas chromatography. Other methods of determination (e.g. spectroscopic methods), optionally also online or inline, can likewise be used in principle, even if they are not preferred. However, the definitive value for the upper limit of the content of aliphatic organic compounds, according to the invention, is the one determined by gas chromatography. In one preferred embodiment, namely work-up by rectification, the stream (d.2) is analysed at the top of the rectification column.

Within the framework of this invention, the word "a/an" in the context of countable quantities is only to be understood as a numeral when this is expressly stated. For example, the expression "a reactor" does not exclude the possibility of the presence of several reactors (connected in series or parallel) within a nitration unit.

An essential feature of the invention is that the content of aliphatic organic compounds in the benzene-containing stream (a.1) or (a.1.1) (so-called 'starting benzene' of the nitration unit or of the first of two nitration units in series) corresponds to the concentrations stated above. In both variants this objective is ultimately achieved by specific removal of the aliphatic organic compounds at at least one point during the process.

In the first variant of the present invention, this removal, which can be performed continuously or discontinuously, is carried out in such a way that the benzene-containing stream (d.2) recycled into step a) of the same nitration unit has a concentration of aliphatic organic compounds which is such that the starting benzene (a.1) satisfies the requirements according to the invention. Details on the arrangement of the specific removal are described below.

In the second variant of the present invention, the aliphatic organic compounds remain predominantly or completely in the benzene-containing stream (d.2.1) of the first nitration unit (100) and are removed with said stream from the first nitration unit (100). This benzene-containing stream (d.2.1) serves as preferably the only component of the starting benzene (a.1.2) of the second nitration unit (200). As essentially only the excess benzene from the first nitration unit (100) is processed in the second nitration unit (200), the latter is substantially smaller than the first nitration unit (100). Here the disadvantages of a possibly increased content of aliphatic organic compounds in the starting benzene are of far less consequence. This procedure makes it possible for the starting benzene (a.1.1) used in the first nitration unit (100) to be exclusively (i.e. without admixtures of 'recycle benzene' that has been recycled) commercially available benzene (provided the latter satisfies the requirements according to the invention in respect of the maximum content of aliphatic organic compounds, although this is generally the case), a procedure which would be uneconomic for the processes known from the state of the art.

Embodiments of both variants are described in greater detail below. Different embodiments can be freely combined with one another so long as those skilled in the art do not perceive an obvious contradiction in the context.

First Variant:

In one embodiment of the process according to the invention, the specific removal of the aliphatic organic compounds takes place in step b). To this end the phase separation in step b) is carried out under conditions such that the aliphatic organic compounds remain predominantly in the gas phase of the phase separation apparatus used and are removed with said phase. The pressure measured relative to atmospheric pressure in the gas phase of the phase separation apparatus ('excess pressure') is therefore adjusted to a value preferably of 20 mbar to 200 mbar, particularly preferably of 30 mbar to 100 mbar, and the temperature in the phase separation apparatus is adjusted to a value preferably of 100° C. to 140° C., particularly preferably of 120° C. to 140° C. This gas phase (hereafter low-boiler stream) is then removed from the process via an off-gas line connected to the gas space of the phase separation apparatus, and treated further. Particularly because of the possibility of the presence of nitrous gases (nitrogen oxides) together with the aliphatic organic compounds, it is preferable to feed an inert gas, preferably nitrogen, into the phase separation apparatus so as to be able effectively to remove the gaseous nitrogen oxides with the low-boiler stream. The invention therefore also provides in particular a process in which an inert gas is fed into the phase separation apparatus in order to assist the removal of the aliphatic organic compounds and optionally nitrogen oxides, the aliphatic organic compounds and optionally nitrogen oxides being removed together with said inert gas via an off-gas line connected to the gas space of the phase separation apparatus.

The nature of the further treatment of the low-boiler stream depends on its composition, i.e. especially the proportion of entrained benzene. If the benzene content is low, the low-boiler stream is preferably burnt. However, if the benzene content of the low-boiler stream is sufficiently high, it may make more economic sense to recover or utilize the benzene it contains. The present invention therefore also provides a process in which all or part of the removed aliphatic organic compounds is worked up by distillation to recover benzene removed together with the aliphatic organic compounds. To this end the low-boiler stream which has been separated off is preferably liquefied by condensation in one or more stages and fed into a phase separation apparatus in order to separate condensed water off at the same time. Preferably, the aliphatic organic compounds are distilled from the resulting organic phase to give benzene as the bottom product stream of the distillation. The recovered benzene is preferably added to the stream (a.1). This procedure is preferred when the benzene content of the low-boiler stream is greater than 50.0 wt %, preferably greater than 70.0 wt %, based in each case on the total weight of the low-boiler stream. The aliphatic organic compounds which have been separated off are preferably burnt or returned to the petrochemical industry. This variant has the advantage that the aliphatic organic compounds which have been separated off do not pass through the work-up in step d). In particular, in the preferred work-up variant, washing with aqueous media and subsequent rectification can give rise to phase separation problems when excessive amounts of aliphatic organic compounds are present, especially in the phase separation of the so-called 'neutral wash' (cf. below under 'step d(iii)' for details). Thus it has been observed that the phase separation time increases sharply when the content of aliphatic organic compounds is too high.

In another embodiment the specific removal of the aliphatic organic compounds takes place in step d). The vapour stream of the benzene rectification column preferably used in step d), comprising benzene, aliphatic organic compounds and residual water, is distilled from the nitrobenzene to give the nitrobenzene product (d.1) as the bottom product stream. The mixture of benzene and aliphatic organic compounds is separated from the residual water. The residual water which has been separated off is recycled for washing. Part of the mixture of benzene and aliphatic organic compounds is removed, preferably from the tank in which the 'recycle benzene' (d.2) is temporarily stored until used, in order to reduce the total amount of aliphatic organic compounds recycled into the process. The removal can be effected continuously or discontinuously, preferably from the tank in which the 'recycle benzene' (d.2) is temporarily stored until used, or from its inlet or outlet lines. The amount of mixture of benzene and aliphatic organic compounds which is to be removed is chosen so as to observe the specification of the starting benzene (a.1) in respect of aliphatic organic compounds, as required according to the invention. The amount of mixture of benzene and aliphatic organic compounds which is to be removed is therefore dependent on the content of aliphatic organic compounds in the fresh benzene fed in. The bulk of the mixture of benzene and aliphatic organic compounds is recycled into the nitration. The removed organic material not recycled into the nitration can be burnt, worked up by distillation to recover benzene or returned to the petrochemical industry. Benzene recovered by distillation is preferably added to the stream (a.1).

The separation of the low boilers can be assisted by using a suitable selectively permeable membrane.

Second Variant:

In the second variant of the process according to the invention, the nitration takes place in a series of two nitration units, the starting benzene used in the second nitration unit (secondary unit, 200) being predominantly or entirely the 'recycle benzene' obtained in the first nitration unit (primary unit, 100).

The first nitration unit (100) preferably comprises several parallel reaction paths, particularly preferably two to four parallel reaction paths. The second nitration unit (200) preferably comprises only one reaction path. The first nitration unit is operated continuously. The second nitration unit can also be operated continuously, but does not have to be. Because of the smaller throughput (the starting benzene of the second nitration unit consists predominantly or entirely of the 'recycle benzene' of the first reaction path, i.e. only the benzene used in stoichiometric excess), the second nitration unit can also be operated discontinuously. In the event of an interruption of production in the second nitration unit during operation of the first nitration unit, the recycle benzene obtained is temporarily stored in a buffer tank.

In the first nitration unit the starting benzene (as distinct from the starting benzene of the second nitration unit denoted by (a.1.1) below; the procedure is analogous for the other process streams) consists of benzene whose content of aliphatic organic compounds is less than 1.5 wt %, preferably less than 0.50 wt %, particularly preferably less than 0.20 wt % and very particularly preferably less than 0.10 wt %, based in each case on the total weight of (a.1.1). It is preferable here to use benzene which has not already been used before as the educt of a nitration (so-called 'fresh benzene'). The addition of 'recycle benzene' is deliberately omitted here. As the content of aliphatic organic compounds in commercially available fresh benzene generally satisfies the requirements according to the invention, it can usually be used direct. However, if the only fresh benzene available is one whose purity does not satisfy the requirements according to the invention, it must be purified, preferably by distillation, before being used in step a) of the first nitration unit. Because of the low content of aliphatic organic compounds in the starting benzene (a.1.1) and the deliberate omission of recycled benzene, the first nitration unit can be operated without problems, even when a specific removal of aliphatic organic compounds in the first nitration unit is omitted, which is a preferred procedure. If however, aliphatic organic compounds are also to be specifically removed in the first nitration unit, this can preferably be carried out as described above for the first variant, namely by removing a low-boiler stream from the gas phase of the phase separation apparatus used in step b). With the exception of the peculiarity of omitting recycle benzene as a component of the starting benzene, the first nitration unit can be operated by any adiabatic nitration process known from the state of the art. The 'recycle benzene' (d.2.1) obtained in step d) of the first nitration unit is not recycled into step a) of the first nitration unit, but is optionally mixed with other benzene, preferably fresh benzene, and used as starting benzene (a.1.2) of the second nitration unit. Meeting the above-defined requirements according to the invention regarding the content of aliphatic organic compounds in the starting benzene (less than 1.5 wt %, preferably less than 0.50 wt %, particularly preferably less than 0.20 wt % and very particularly preferably less than 0.10 wt %, based in each case on the total weight of the starting benzene) is not essential for the starting benzene (a.1.2) of the second nitration unit. With the exception of this peculiarity, the second nitration unit can be operated by any adiabatic nitration process known from the state of the art. The crude nitrobenzene (b.2.2) obtained in the second nitration unit after separation of the aqueous phase comprising sulfuric acid (b.1.2) in a phase separation apparatus is preferably combined with the crude nitrobenzene (b.2.1) of the first nitration unit, and together they are worked up further in steps c) and d). In this preferred arrangement of the variant with two nitration units, thus there is only one 'recycle benzene stream' (d.2) from step d), which originates from the distillation of the combined crude nitrobenzene streams (b2.1) and (b.2.2). In this embodiment—with the exception of a non-specific removal which always occurs to a certain extent via the off-gas and therefore also takes place in the first nitration unit—the specific removal of the aliphatic organic compounds from the first nitration unit (100) is effected via the removal (rather than the otherwise conventional recycling) of the 'recycle benzene' (d.2.1). Different possibilities are available for the arrangement of the removal of aliphatic organic compounds from the second nitration unit:

Before being combined with the crude nitrobenzene (b.2.1) of the first nitration unit, the crude nitrobenzene (b.2.2) from the second nitration unit can be freed of aliphatic organic compounds and excess benzene in a distillation column. Because of the possibility of acid residues being present in the stream (b.2.2), such a distillation column is preferably of corrosion-resistant design. The low-boiler stream obtained here, consisting of aliphatic organic compounds and excess benzene, can be treated further in a variety of ways. If the benzene content is low, the low-boiler stream is preferably burnt. If the benzene content of the low-boiler stream is sufficiently high, however, it may make more economic sense to recover or utilize the benzene it contains. The present invention therefore also provides a process in which all or part of the removed aliphatic organic compounds is worked up by distillation to recover benzene removed together with the aliphatic organic compounds. The aliphatic organic compounds are preferably distilled off to give benzene as the bottom product stream of the distillation. The recovered benzene is preferably added to the stream (a.1.1). This procedure is preferred when the benzene content of the low-boiler stream is greater than 50.0 wt, preferably greater than 70.0 wt % based in each case on the total weight of the low-boiler stream. The aliphatic organic compounds which have been separated off are preferably burnt Very particularly preferably, this low-boiler stream is returned to the fresh benzene supplier. Because the second nitration unit is appreciably less sensitive to increased contents of aliphatic organic compounds, there is the further possibility of using at least part of the low-boiler stream as is, i.e. without distillative separation into aliphatic organic compounds and benzene, as an additional component of the starting benzene (a.1.2).

In principle, the different options of specifically removing aliphatic organic compounds described above for the first variant can also be used in the nitration unit (200) of the second variant. However, this is not essential as the adverse effect of any increased contents of aliphatic organic compounds is far less substantial in the small secondary unit (200) than in the primary unit (100).

One possible embodiment of the second variant is illustrated in greater detail below with the aid of FIG. 2 attached:
First Nitration Unit (Primary Unit)

A sulfuric acid stream (11)=(a.2.1), a nitric acid stream (12)=(a.3.1) and a fresh benzene stream (13)=(a1.1) are fed into a reactor (1). Once all the nitric acid has reacted with the benzene to give nitrobenzene under adiabatic reaction conditions, the reaction product (14), now at a temperature of approx. 130° C., is fed into a phase separation apparatus (2), in which the reaction product (14) separates into an organic phase ((15)=(b.2.1)=crude nitrobenzene, comprising benzene and low boilers in addition to nitrobenzene) and an aqueous phase ((16)=(b.1.1)=waste acid, still comprising small proportions of nitrobenzene and benzene in addition to sulfuric acid). The aqueous phase (16), comprising mainly sulfuric acid, is subjected to a flash evaporation of water in the evaporator (3) by sudden pressure reduction, and is thereby concentrated. The concentrated sulfuric acid (17) is stored in the sulfuric acid tank (4) until it is re-used. After separation in the phase separation apparatus, the crude nitrobenzene (15)= (b.2.1) is cooled to approx. 50° C. in the crude nitrobenzene cooler (5) and fed into the washer (6).

The resulting stream of pre-purified nitrobenzene (18), substantially freed of nitrophenols and salts, is heated again and, in a distillation column (7), freed of water, benzene and low boilers that are still present, which are separated off (19) at the top, to give pure nitrobenzene (20)=(d.1.1), which is stored in a tank (8). The condensed top product (19) of the distillation column (7) is fed into a phase separation apparatus (9), in which the top product separates into an organic phase ((21)=(d.2.1), comprising benzene) and an aqueous phase (22). The organic phase (21)=(d.2.1) is led into a tank (10).
Second Nitration Unit (Smaller, Single-Path Secondary Unit)

A sulfuric acid stream (11*)=(a.2.2), a nitric acid stream (12*)=(a.3.2), optionally a fresh benzene stream (13*) and the organic phase (21)=(d.2.1) from the tank (10) are fed into a reactor (1*). Once all the nitric acid has reacted with the benzene to give nitrobenzene under adiabatic reaction conditions, the reaction product (14*), now at a temperature of approx. 130° C., is fed into a phase separation apparatus (2*), in which the reaction product (14*) separates into an organic phase ((15*)=(b.2.2)=crude nitrobenzene, comprising benzene and low boilers in addition to nitrobenzene) and an aqueous phase ((16*)=(b.1.2)=waste acid, still comprising small proportions of nitrobenzene and benzene in addition to sulfuric acid). The aqueous phase (16*)=(b.1.2), comprising mainly sulfuric acid, is combined with the phase (16)=(b.1.1), comprising mainly sulfuric acid, of the upstream nitration of fresh benzene in the first nitration unit, and together they are subjected to a flash evaporation of water in the evaporator (3) by sudden pressure reduction, and are also thereby concentrated. The concentrated sulfuric acid (17) is stored in the sulfuric acid tank (4) until it is re-used. After separation in the phase separation apparatus (2*), the crude nitrobenzene (15*)=(b.2.2) is freed of low boilers and a proportionate amount of benzene in a distillation column (7*). This can be done by direct or indirect heating with steam. The bottom product (24)=(b.2.2), poor in aliphatic organic compounds and comprising nitrobenzene, which was not withdrawn at the top of the distillation column (7*), is combined with the crude nitrobenzene stream (15)=(b.2.1), and together they are cooled to approx. 50° C. in the crude nitrobenzene cooler (5) and fed into the washer (6). In this variant there is thus no recycle benzene stream in the classical sense. However, there is a recycle benzene stream (d.2)=(21) from step d), which originates from the distillation of the combined crude nitrobenzene streams (b.2.1)=(15) and (b.2.2)=(24) and is processed in the second nitration unit. The top product (23) (the low-boiler stream) of the distillation column (7*) is temporarily stored in the buffer tank (25).

In all the embodiments it is additionally possible for fractions of the aliphatic organic compounds to be removed via the off-gas of the other operating units, such as washing and distillation units, etc., of a nitration unit.

In all the embodiments of the process according to the invention, the specific removal of the aliphatic organic compounds is preferably arranged in such a way that the content of aliphatic organic compounds in the recycle benzene (d.2) is from 0.1 wt % to 60.0 wt %, particularly preferably from 0.1 wt % to 40.0 wt %, very particularly preferably from 0.1 wt % to 20.0 wt % and extremely particularly preferably from 0.0001 wt % to 10.0 wt %, based in each case on the total weight of (d.2).

The steps of the invention, which are the same for both variants and all the aforementioned embodiments of the specific removal of the aliphatic organic compounds, are illustrated in detail below. Different embodiments can be freely combined with one another so long as those skilled in the art do not perceive an obvious contradiction in the context.

In principle, step a) can be carried out by any of the adiabatic nitration processes known from the state of the art, provided they make it possible to observe the specified boundary conditions regarding the benzene excess and the purity of the starting materials. This step of the process according to the invention is preferably executed using a tubular reactor in which several dispersing elements are distributed over the length of the reactor to ensure intensive dispersion and intermixing of the benzene, nitric acid and sulfuric acid. Such a reactor, and the shape of dispersing elements which can be used, are described e.g. in EP 0 708 076 B1 (FIG. 2) and EP 1 291 078 A2 (FIG. 1). Step a) is preferably executed by a procedure such as that described in DE 10 2008 048 713 A1, especially paragraph [0024].

The phase separation in step b) is also carried out by methods known per se from the state of the art, in a separation tank familiar to those skilled in the art. The aqueous phase (b.1) comprises essentially sulfuric acid (diluted due to the formation of water of reaction and the entrainment of water into the reaction from the nitric acid used) together with inorganic impurities; the organic phase (b.2) comprises essentially nitrobenzene together with excess benzene and organic impurities.

In principle, the concentration of the aqueous phase (b.1) in step c) is effected in the manner known from the state of the art. The sulfuric acid in the aqueous phase is concentrated in a flash evaporator by evaporating water into a region of reduced pressure. If the reaction conditions in the adiabatic nitration of benzene with mixed acid are chosen correctly, the heat of the exothermic reaction heats the aqueous phase (b.1) comprising sulfuric acid to a sufficient extent that the concentration and temperature of the aqueous phase comprising sulfuric acid in the flash evaporator can simultaneously be restored to the concentration and temperature of said phase as it entered the reaction space prior to the reaction with benzene and nitric acid, i.e. (c.1) corresponds to (a.2) in terms of temperature and concentration. This is described in EP 2 354 117 A1, especially paragraph [0045].

In principle, the work-up of the organic phase (b.2) in step d) is effected in the manner known from the state of the art. A preferred procedure is described below:

The organic phase (b.2), which usually still contains traces of acid, is washed in one or two washes, preferably one wash, with an aqueous wash liquor and then separated from the acidic aqueous phase by phase separation (in the case of several washes, after each individual wash). The acid residues contained in the crude nitrobenzene (b.2) are washed out in this process, so this process step is also referred to as an acid wash. This step is sufficiently well known from the state of the art and is therefore only briefly outlined here. Preferably, aqueous streams obtained during the operation are recycled for the purpose of carrying out this acid wash. (Step d(i).)

The resulting organic phase is then washed in one or two alkaline washes, preferably one wash, with an aqueous solution of a base preferably selected from sodium hydroxide, sodium carbonate or sodium hydrogen carbonate, and then separated from the alkaline wash water by phase separation (in the case of several washes, after each individual wash). Particularly preferably, sodium hydroxide solution is used as the aqueous base solution. This step is sufficiently well known from the state of the art and is therefore only briefly outlined here. The pH of the sodium hydroxide solution used and its weight ratio to the organic phase are adjusted so that acidic impurities (e.g. nitrophenols formed as by-products and acid residues not completely removed in step d(i)) are substantially or fully neutralized, preferably fully neutralized, in this/these alkaline wash(es). The subsequent work-up of the alkaline effluent can be effected by the processes of the state of the art, e.g. according to EP 1 593 654 A1 and EP 1 132 347 A2. (Stop d(ii).)

Finally, the resulting organic phase is washed with water in at least one, preferably two to four, particularly preferably two or three and very particularly preferably two neutral washes, and then separated from the aqueous phase by phase separation (in the case of several washes, after each individual wash). In principle, this can be carried out by any of the processes conventionally used in the state of the art. The wash water used here is preferably demineralized water, particularly preferably a mixture of demineralized water and vapour condensate (i.e. a condensate of water vapour which has been obtained by heat exchange between water and any exothermic process steps) and very particularly preferably vapour condensate. A preferred procedure is one in which electrophoresis is employed in the last neutral wash (cf. WO 2012/013678 A2). (Step d(iii).)

The washed nitrobenzene is finally freed of dissolved water, unreacted benzene and optionally organic impurities by further work-up. This work-up is preferably effected by distillation, the vapours of water, benzene and optionally organic impurities being driven off at the top. The vapours are cooled and led into a separation tank. Water settles out in the lower phase and is separated off. The upper phase comprises benzene and low boilers, which are recycled into the reaction as recycle benzene (d.2). A rectification column is preferably used as the distillation apparatus. The bottom product of the distillation, optionally after a further distillation in which nitrobenzene is obtained as distillate (i.e. as top or side stream product), is used as pure nitrobenzene (d.1) for other purposes (such as hydrogenation to aniline). (Step d(iv).)

If the content of aliphatic organic compounds in the starting benzene (a.1 or a.1.1) is minimized, the following advantages are gained:

i) The crude nitrobenzene poor in aliphatic organic compounds which is obtained in the separation tank of step b) needs less cooling medium for cooling prior to entering the acid wash.

ii) The heating of the crude nitrobenzene poor in aliphatic organic compounds, as required in the distillation after the wash, needs less heating medium.

iii) The formation of reaction by-products such as picric acid is minimized.

iv) The sulfuric acid losses in the acid wash are smaller.

v) The nitration of benzene free of aliphatics has the additional advantage that the hydraulic loading in the reaction is smaller, so the available production capacity is higher.

vi) Phase separation problems in step d(iii) are minimized by shortened phase separation times, reducing the capital expenditure for an apparatus.

vii) The formation of reaction by-products such as nitrogen oxides ($NO_x$) is minimized.

In the preparation of nitrobenzene by the adiabatic nitration of benzene with the continuous or discontinuous discharge of aliphatic organic compounds from the process cycle, a higher plant productivity, lower energy costs and a better product quality are achieved when the nitration is carried out with starting benzene that satisfies the specification according to the invention.

EXAMPLES

Unless indicated otherwise, contents in ppm or % are by weight, based on the total weight of the material (material stream) in question. Analytical values were determined by gas chromatography.

Examples 1 to 5

The nitration was carried out by a process as shown in FIG. 1. FIG. 1 shows a process in which only the first nitration unit (primary unit) of FIG. 2 is used. The reference numbers of FIG. 1 have the same meaning as that illustrated above for the primary unit of FIG. 2. The fresh benzene comprised aliphatic organic compounds (hereafter aliphatics) in the range from 200 ppm to 2000 ppm. The stoichiometric excess of benzene, based on nitric acid, was adjusted to values of 4.0% to 10% of theory. The recycle benzene (21)=(d.2) comprised from 10 wt % to 50 wt % of aliphatics, based on the total weight of the recycle benzene. The aliphatics content of the starting benzene is made up of the particular aliphatics content of the fresh benzene and the corresponding aliphatics content of the recycle benzene. It is found that the sulfuric acid loss and the picric acid values rise as the aliphatics content of the starting benzene increases. The aliphatics were removed in the phase separation apparatus under an excess nitrogen pressure of 53 mbar. The temperature of the nitrating solution was 130° C. to 133° C. The off-gas from the phase separation apparatus was condensed in one stage.

Example 6

Figure 2:
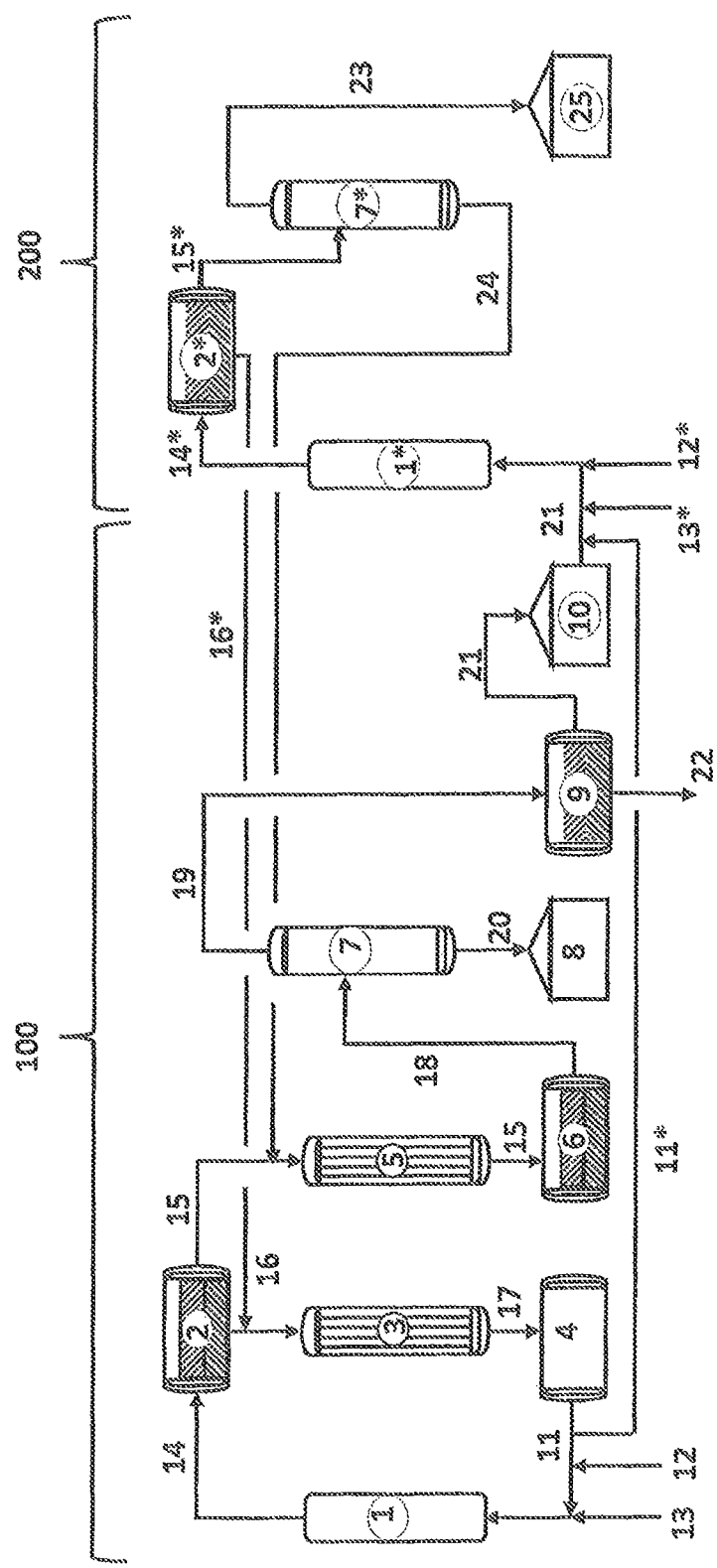
FIG. 2 illustrates one possible embodiment of the second variant of the present invention.

The nitration was carried out in a first nitration unit (the primary unit), with a second, downstream nitration unit (the secondary unit), by a process as shown in FIG. 2.

The primary unit was operated exclusively with fresh benzene (13) comprising 1013 ppm of aliphatic organic compounds (hereafter aliphatics). The resulting recycle benzene (21)=(d.2.1) comprised approx. 1.818 wt % of aliphatics, based on the total weight of the recycle benzene, and was fed into the reaction (1*) of the secondary unit. A sulfuric acid stream (11*)=(a.2.2) and a nitric acid stream (12*)=(a.3.2) were also fed into the reactor (1*) of the secondary unit. The stoichiometric excess of benzene, based on nitric acid, was adjusted to values of 4.0% to 10% of theory in the primary and secondary units. It is found that in the primary unit, with the very low content of approx. 1000 ppm of aliphatics in the starting benzene, the sulfuric acid losses are only very small and the picric acid values in the crude nitrobenzene are very low. In the secondary unit the recycled sulfuric acid was separated off as the lower phase (16*) in the phase separation apparatus (2*), combined with the recycled sulfuric acid from the primary unit (stream 16) and concentrated in the evaporator (3) of the primary unit. The upper, organic phase in the separation apparatus was led into the distillation column (7*) of the secondary unit, in which the nitrobenzene was freed of benzene, aliphatics and traces of water and recycled as the stream (24) into the primary unit, where it was combined with the crude nitrobenzene (stream 15) and cooled in the heat exchanger (5) of the primary unit. The vapours from the distillation column were freed of water in a phase separation apparatus and the organic phase (23) was led into a buffer tank (25).

Examples 1 to 6 are described in Table 1 below.

TABLE 1

| Example | Benzene excess [% of theory, based on nitric acid][a] | Aliphatics content of fresh benzene[a] [ppm] | Aliphatics content of recycle benzene fed into reactor 1 [%] | Aliphatics content of starting benzene of reactor 1 [%] | Sulfuric acid loss via stream 15[c] [%] | Picric acid content of stream 15 [ppm] |
|---|---|---|---|---|---|---|
| 1 (comparative) | 5.565 | 788 | 48 | 4.43527 | 1.7 | 431 |
| 2 (comparative) | 4.880 | 894 | 41 | 3.11981 | 1.5 | 357 |
| 3 (comparative) | 5.612 | 993 | 31 | 2.38824 | 1.0 | 228 |
| 4 (according to the invention) | 6.502 | 975 | 19 | 1.49768 | 0.5 | 95 |
| 5 (according to the invention) | 5.231 | 953 | 12 | 0.76915 | 0.4 | 113 |
| 6 (according to the invention), with primary and secondary units (without recycle benzene in the primary unit) | 5.899 | 1013 | — (no recycle benzene stream in reactor 1 (primary unit)) | 0.1013 | 0.3 | 87 |

[a]In Example 6 the data apply to both primary and secondary units.
[b]The aliphatics content of the starting benzene of reactor 1* (Example 6, secondary unit) was 1.818 wt %.
[c]If the aliphatics content of stream 14 is too high, its low boiling point can cause "bubbling" in the phase separation apparatus 2. Hence sulfuric acid enters the organic phase, stream 15, and is lost in the wash instead of being recycled via stream 16.

The examples show that the process according to the invention can minimize the sulfuric acid losses and markedly reduce the picric acid content of the crude nitrobenzene.

Example 7

Illustration of the Relationship Between Phase Separation and Aliphatics Content To study the influence of the aliphatics content on the phase separation of a mixture of nitrobenzene, optionally benzene and aliphatics, aliphatics were added to nitrobenzene and nitrobenzene/benzene mixtures up to a content of 3.89 wt %, based in each case on the total weight of the organic mixture. The aliphatics content of the nitrobenzene used was negligibly small (<100 ppm) and was therefore ignored in subsequent considerations. The nitrobenzene was free of nitrophenols and acid. The case reworked was consequently that of a neutral wash of crude nitrobenzene (step d(iii)). By varying the aliphatics content, it was possible to test whether a prior separation of aliphatics makes itself noticeable in the wash.

Example 7a

Nitrobenzene and demineralized water (weight ratio of organic phase to demineralized water=2.8) were stirred in a heatable separating funnel with a disk-type agitator for 10 min at 40° C. and 600 rpm. The stirrer was then stopped and the time taken for complete phase separation was measured.

Example 7b

Nitrobenzene, benzene (8.74% of the weight of the nitrobenzene) and demineralized water (ratio of organic phase to demineralized water=2.8) were stirred in a heatable separating funnel with a disk-type agitator for 10 min at 40° C. and 600 rpm. The stirrer was then stopped and the time taken for complete phase separation was measured.

Examples 7c and 7d

Nitrobenene, a benzene/aliphatics mixture and demineralized water (ratio of organic phase to demineralized water=2.8) were stirred in a heatable separating funnel with a disk-type agitator for 10 min at 40° C. and 600 rpm. The stirrer was then stopped and the time taken for complete phase separation was measured.

The results in Table 2 show that a low content of aliphatics in the neutral wash has a positive effect on the phase separation time, so it is possible to reduce the size of the tank required for the phase separation, even if only part of the aliphatics is separated off.

TABLE 2

Phase separation times in the washing of nitrobenzene/benzene/aliphatics mixtures with demineralized water

| Example | Nitro-benzene [g] | Benzene [g] | Added aliphatics [g] | Added aliphatics [%] | Aliphatics content of recycle benzene [%][a] | Phase separation time [sec] |
|---|---|---|---|---|---|---|
| 7a | 299.98 | 0 | 0 | 0 | — | 16 |
| 7b | 299.97 | 26.22 | 0 | 0 | 0 | 18 |
| 7c | 299.95 | 24.82 | 1.16 | 0.36 | 4.46 | 21 |
| 7d | 299.99 | 20.99 | 4.92 | 1.51 | 18.99 | 27 |
| 7e | 299.98 | 20.88 | 12.47 | 3.72 | 37.39 | 42 |

[a]calculated for the case where all the benzene contained in the mixture of nitrobenzene, optionally benzene and aliphatics is fed to a nitration process.

The results show that the phase separation time increases with the aliphatics content.

The invention claimed is:

1. A continuous adiabatic process for the preparation of nitrobenzene by the nitration of benzene in a nitration unit, comprising:
  a) reacting a benzene-containing stream (a.1), comprising at least 90 wt % of benzene, based on the total weight of (a.1), in a reactor with a mixture of sulfuric acid (a.2) and nitric acid (a.3) under adiabatic conditions, the benzene being used in a stoichiometric excess, based on nitric acid (a.3),
  b) separating the process product obtained in step a) in a phase separation apparatus into an aqueous phase (b.1) comprising sulfuric acid and an organic phase (b.2) comprising nitrobenzene,
  c) concentrating the aqueous phase (b.1) obtained in step b) by evaporation of the water to give an aqueous phase (c.1) having a higher sulfuric acid concentration than (b.1), and recycling all or part of the phase (c.1) into step a) and using the phase (c.1) as a component of (a.2), and
  d) working up the organic phase (b.2) obtained in step b) to pure nitrobenzene (d.1) to give a benzene-containing stream (d.2), all or part of which is used as a component of (a.1) in the nitration unit of step a),
  wherein
  aliphatic organic compounds are specifically removed from the process at at least one point so that only such a benzene-containing stream (a.1) having a content of aliphatic organic compounds of less than 1.5 wt %, based on the total weight of (a.1), is fed into the reactor.

2. An adiabatic process for the preparation of nitrobenzene by the nitration of benzene in a series of two nitration units (100, 200) each having at least one reactor (1, 1*), comprising:
  a) reacting exclusively benzene (a.1.1) having a content of aliphatic organic compounds of less than 1.5 wt %, based on the total weight of (a.1.1), in the reactor (1) of the first, continuously operating nitration unit (100) with a mixture of sulfuric acid (a.2.1) and nitric acid (a.3.1) under adiabatic conditions, the benzene being used in a stoichiometric excess, based on nitric acid (a.3.1),
  b) separating the process product obtained in step a) in a phase separation apparatus (2) into an aqueous phase (b.1.1) comprising sulfuric acid and an organic phase (b.2.1) comprising nitrobenzene,
  c) concentrating the aqueous phase (b.1.1) obtained in step b) by evaporation of the water to give an aqueous phase (c.1.1) having a higher sulfuric acid concentration than (b.1.1), and recycling all or part of the phase (c.1.1) into step a) and using the phase (c.1.1) as a component of (a.2.1), and
  d) working up the organic phase (b.2.1) obtained in step b) to pure nitro-benzene (d.1.1) to give a benzene-containing stream (d.2.1),
  and reacting the benzene-containing stream (d.2.1) in a reactor (1*) of the second, continuously or discontinuously operating nitration unit (200) with a mixture of sulfuric acid (a.2.2) and nitric acid (a.3.2) under adiabatic conditions to give nitrobenzene, the benzene being used in, a stoichiometric excess, based on nitric acid (a.3.2), of 2.0% to 20%, of theory, and then working up the nitrobenzene formed thereby to pure nitrobenzene.

3. The process according to claim 1, wherein the aliphatic organic compounds are selected from the group consisting of cyclohexane, heptane, methylcyclohexane, bicycloheptane, isomers of dimethylcyclopentane, ethylcyclopentane, pentane, cyclopentane and 2-methylhexane.

4. The process according of claim 1, wherein the pressure measured relative to atmospheric pressure in the gas phase of the phase separation apparatus used in step b) is adjusted to a value of 20 mbar to 200 mbar, wherein the temperature in the phase separation apparatus used in step b) is adjusted to a value of 100° C. to 140° C., and wherein aliphatic organic compounds are removed with the gas phase of the phase separation apparatus used in step b).

5. The process according to claim 4, further comprising feeding an inert gas into the phase separation apparatus in order to assist the removal of the aliphatic organic compounds, the aliphatic organic compounds being removed together with said inert gas via an off-gas line connected to the gas space of the phase separation apparatus.

6. The process according to claim 2, further comprising separating the process product obtained in the adiabatic reaction in the reactor (1*) in a phase separation apparatus (2*) into an aqueous phase (b.1.2) comprising sulfuric acid and an organic phase (b.2.2) comprising nitrobenzene, and the organic phase (b.2.2)=(15*) being freed of aliphatic organic compounds and excess benzene in a distillation column (7*) and then mixed with the organic phase (b.2.1)=(15) of the first nitration unit (100).

7. The process according to claim 1, further comprising working up all or part of the removed aliphatic organic compounds by distillation to recover benzene removed together with the aliphatic organic compounds.

8. The process according to claim 7, further comprising using all or part of the recovered benzene as a component of the stream (a.1) or (a.1.1).

9. The process according to claim 2 wherein the aliphatic organic compounds are selected from the group consisting of cyclohexane, heptane, methylcyclohexane, bicycloheptane, isomers of dimethylcyclopentane, ethylcyclopentane, pentane, cyclopentane and 2-methylhexane.

10. The process according to claim 2, wherein the pressure measured relative to atmospheric pressure in the gas phase of the phase separation apparatus used in step b) is adjusted to a value of 20 mbar to 200 mbar, wherein the temperature in the phase separation apparatus used in step b) is adjusted to a value of 100° C. to 140° C., and wherein aliphatic organic compounds are removed with the gas phase of the phase separation apparatus used in step b).

11. The process according to claim 10, further comprising feeding an inert gas into the phase separation apparatus in order to assist the removal of the aliphatic organic compounds, the aliphatic organic compounds being removed together with said inert gas via an off-gas line connected to the gas space of the phase separation apparatus.

12. The process according to claim 9, further comprising separating the process product obtained in the adiabatic reaction in the reactor (1*) in a phase separation apparatus (2*) into an aqueous phase (b.1.2) comprising sulfuric acid and an organic phase (b.2.2) comprising nitrobenzene, and the organic phase (b.2.2)=(15*) being freed of aliphatic organic compounds and excess benzene in a distillation column (7*) and then mixed with the organic phase (b.2.1)=(15) of the first nitration unit (100).

13. The process according to claim 10, further comprising separating the process product obtained in the adiabatic reaction in the reactor (1*) in a phase separation apparatus (2*) into an aqueous phase (b.1.2) comprising sulfuric acid and an organic phase (b.2.2) comprising nitrobenzene, and the organic phase (b.2.2)=(15*) being freed of aliphatic organic compounds and excess benzene in a distillation column (7*) and then mixed with the organic phase (b.2.1)=(15) of the first nitration unit (100).

14. The process according to claim 11, further comprising separating the process product obtained in the adiabatic reaction in the reactor (1*) in a phase separation apparatus (2*) into an aqueous phase (b.1.2) comprising sulfuric acid and an organic phase (b.2.2) comprising nitrobenzene, and the organic phase (b.2.2)=(15*) being freed of aliphatic organic compounds and excess benzene in a distillation column (7*) and then mixed with the organic phase (b.2.1)=(15) of the first nitration unit (100).

15. The process according to claim 2, wherein the benzene is used in a stoichiometric excess, based on nitric acid (a.3.2), of 5.0% to 10% of theory.

* * * * *